United States Patent [19]
Boussignac et al.

[11] Patent Number: 6,030,362
[45] Date of Patent: Feb. 29, 2000

[54] CATHETER FOR THE DELIVERY OF A THERAPEUTICALLY ACTIVE SUBSTANCE

[75] Inventors: Georges Boussignac, Antony; Vincent Lagarde, Paris, both of France

[73] Assignee: Laboratories Nycomed SA, Paris Cedex, France

[21] Appl. No.: 09/171,473

[22] PCT Filed: May 6, 1997

[86] PCT No.: PCT/FR97/00799

§ 371 Date: Oct. 19, 1998

§ 102(e) Date: Oct. 19, 1998

[87] PCT Pub. No.: WO97/41915

PCT Pub. Date: Nov. 13, 1997

[30] Foreign Application Priority Data

May 6, 1996 [FR] France .................................. 96 05615

[51] Int. Cl.⁷ .................................................. A61M 29/00
[52] U.S. Cl. ........................... 604/101; 604/96; 604/916; 604/919
[58] Field of Search ..................... 604/96, 101, 915–917, 604/919, 921; 606/192–194

[56] References Cited

U.S. PATENT DOCUMENTS

| | | | |
|---|---|---|---|
| 4,762,130 | 8/1988 | Fogarty et al. ....................... | 128/348.1 |
| 4,934,786 | 6/1990 | Krauter ................................... | 604/101 |
| 5,226,888 | 7/1993 | Arney ..................................... | 604/96 |
| 5,250,070 | 10/1993 | Parodi . | |
| 5,252,159 | 10/1993 | Arney ..................................... | 156/169 |
| 5,304,132 | 4/1994 | Jang . | |
| 5,308,356 | 5/1994 | Blackshear, Jr. et al. .............. | 604/194 |
| 5,383,856 | 1/1995 | Bersin ..................................... | 604/101 |
| 5,415,634 | 5/1995 | Glynn et al. .............................. | 604/96 |
| 5,484,411 | 1/1996 | Inderbitzen et al. ....................... | 604/96 |
| 5,545,134 | 8/1996 | Hilaire et al. . | |
| 5,716,340 | 2/1998 | Schweich, Jr. et al. ................. | 604/101 |
| 5,749,852 | 5/1998 | Schwab et al. ............................ | 604/96 |
| 5,797,948 | 8/1998 | Dunham .................................. | 606/194 |
| 5,810,767 | 9/1998 | Klein ......................................... | 604/96 |
| 5,891,091 | 4/1999 | Teirstein .................................. | 604/104 |
| 5,902,266 | 5/1999 | Leone et al. ............................. | 604/53 |

FOREIGN PATENT DOCUMENTS

| | | |
|---|---|---|
| 0 275 230 A2 | 7/1988 | European Pat. Off. . |
| 0 414 350 A1 | 2/1991 | European Pat. Off. . |
| 0 526 102 | 2/1993 | European Pat. Off. . |
| WO 95/28197 | 10/1995 | WIPO . |
| WO 96/18427 | 6/1996 | WIPO . |

*Primary Examiner*—Wynn Wood Coggins
*Assistant Examiner*—Sharon Finkel
*Attorney, Agent, or Firm*—Merchant & Gould

[57] ABSTRACT

The invention features a catheter particularly for the delivery of a therapeutically active substance comprising a catheter body and an inflatable structure comprising three inflatable elements and a diaphragm fixed to these elements and defining with them, a passage duct for the body fluid and a sealed cavity to contain a therapeutically active substance. The said first (3), second (4) and third (7) inflatable elements are made of one preformed piece consisting of a helically coiled tube, said third element (7) being constituted by one or more turns of the coil, the diameter of the said tube at the portion constituting the third element being less than the diameter of the said tube at the tube portions constituting the said first and second elements respectively and intended to rest against the internal wall of said body duct; the said catheter body is disposed inside the coil of the said tube, in the aforementioned duct. This invention is useful in the preventive treatment of restenosis.

19 Claims, 4 Drawing Sheets

CATHETER FOR THE DELIVERY OF A THERAPEUTICALLY ACTIVE SUBSTANCE

FIELD OF THE INVENTION

The subject of the present invention is a catheter intended to be introduced into a bodily canal in which a fluid flows, particularly in order to deliver thereto a therapeutically active substance in a localised region of said canal, without interrupting the flow of said fluid.

The main application of the invention is in the field of treating blood vessels and, even more particularly, in the treatment of restenosis.

The catheter according to the present invention may, however, be used for treating a variety of disorders of various morphological canals in the human or animal body, such as, in particular, the urinary canals and, in particular, the urethra, or else the digestive canals and, in particular, the oesophagus.

This catheter is mainly intended for locally delivering a therapeutically active substance, but also enables isolating a segment of the wall of a bodily canal, for example for assisting a surgical operation upon said wall segment thus isolated.

In order to clarify the explanation, the catheter according to the present invention will be described in its preferred particular application to the preventive treatment of restenosis.

BACKGROUND OF THE INVENTION

It is known that restenosis can be defined as a recurrent reduction in the calibre of the coronary lumen at the site initially expanded with success during a coronary transluminal angioplasty.

This disorder remains the main current limitation on balloon coronary angioplasty since it leads to a new angioplasty in approximately 15 to 30% of cases within the 6 months following a successful angioplasty.

Various solutions have been envisaged to date for the prevention of restenosis, and these have led to more or less satisfactory results.

Thus, the use of so-called "ablative" angioplasty techniques such as, for example, laser angioplasty or atherectomy have not permitted a significant reduction in the incidence of restenosis.

In contrast, fitting a coronary endoprosthesis after angioplasty constitutes a relatively effective treatment in the prevention of restenosis, since it leads to a reduction by approximately 30% in the risk of restenosis.

However, the systematic fitting of endoprostheses cannot be envisaged, insofar as this could lead to operating unnecessarily on a large number of patients who would have suffered no restenosis without an endoprosthesis, and insofar as there would still be a relatively large number of patients suffering restenosis in spite of the fitting of an endoprosthesis.

Systemic administration of pharmacologically active substances such as antithrombins, converting enzyme inhibitors, some vasodilators or some hypolipidemic agents has to date not led to entirely satisfactory results.

This is why the use of devices intended for local delivery of therapeutically active substances constitutes a more promising prospect in the prevention of restenosis.

In fact, this method makes it possible to administer, at the dilated site, products which are specifically targeted against the mechanisms of restenosis, including products which are toxic for the rest of the body, in predetermined concentrations and over a variable period of time.

In order to be usable in the context of this method, the device must permit local delivery of the active substance without interruption to the flow of fluid in the bodily canal.

A catheter satisfying this requirement has been proposed in the document EP 0.526.102.

This catheter is generally composed of an elongate tubular element including an inflatable structure arranged at its distal part.

This inflatable structure consists of a set of identical toric balloons and a membrane fixed to these balloons, this structure being designed in such a way that, when it is inflated, it defines:

on the one hand, a central passage channel for the bodily fluid; and on the other hand, a substantially leaktight cavity or pouch, intended to contain said therapeutically active substance and defined by the balloons, by the outer surface of the membrane and by the inner surface of the bodily canal.

The catheter body includes a first internal channel which communicates, on the one hand, with the balloons and, on the other hand, with a means making it possible to inflate and deflate these balloons; and a second internal channel which communicates, on the one hand, with the aforementioned cavity and, on the other hand, with a supply source of fluid containing a pharmacologically active substance.

As can be seen in the aforementioned document, in the diagrams illustrating the various embodiments of this catheter, the catheter body as well as the various intermediate balloons intended for holding the membrane in position are in direct contact with the bodily canal.

The result of this is that such a device does not make it possible to treat effectively, that is to say in a single operation, the entire surface of the bodily canal at the dilated site, since the active substance cannot reach the portion of the surface of the bodily canal which is in contact with the balloons and the catheter body, unless the inflatable structure is displaced, and this complicates the operation.

SUMMARY OF THE INVENTION

The object of the present invention is to solve this technical problem by providing a novel design of catheter which is simpler to produce and fit, and which makes it possible to deliver a therapeutically active substance in a single operation over the entire surface of the bodily canal to be treated.

The solution according to the present invention, for solving this technical problem, consists of a catheter intended to be introduced into a bodily canal in which a fluid flows, particularly in order to deliver thereto, in a localised region, a therapeutically active substance carried by a second fluid, of the type comprising:

a catheter body including an elongate tubular element having a proximal part and a distal part;

an inflatable structure, arranged at the distal part of said catheter body and including:

a first inflatable element and a second inflatable element which, when inflated:

are axially separated from one another;

each bear in leaktight fashion against the internal wall of the said bodily canal; and each has a substantially central opening;

a membrane, fixed to said first and second inflatable elements and defining with them, when they are inflated;

on the one hand, a substantially cylindrical sleeve, joining together the central openings of the said first and second inflatable elements, in leaktight fashion, thus forming a channel for passage of the bodily fluid; and on the other hand, a substantially leaktight cavity, capable of containing said therapeutically active substance and defined by said first and second inflatable elements, by the external surface of said membrane and by the internal surface of the bodily canal;

a third inflatable element, arranged between said first and second inflatable elements, designed to keep said membrane in position when it is inflated;

said catheter body including a first internal channel which communicates, on the one hand, with said first, second and third inflatable elements and, on the other hand, with a means making it possible to inflate and deflate these elements; and a second internal channel which communicates on the one hand, with the aforementioned cavity and, on the other hand, with a supply source of fluid containing said pharmacologically active substance, and optionally a third internal channel, independent from said second internal channel, which communicates on the one hand with the aforementioned cavity, and on the other hand, with a supply source of fluid optionally containing a therapeutically active substance, or with a suction device, characterised in that said first, second and third inflatable elements are made in a single preformed part, consisting of a helically wound tube, said third element consisting of one or more turns of this winding, the diameter of said tube at the portion constituting said third element being less than the diameter of said tube at the tube portions which respectively constitute said first and second elements and are intended to bear against the internal wall of said bodily canal; and characterised in that said catheter body is arranged inside the winding of said tube, in the aforementioned central channel.

Thus, as will be understood, the originality of the present invention resides in the fact that neither the catheter body nor the third inflatable element intended to hold the membrane in position are directly in contact with the internal surface of the morphological canal, which makes it possible to treat, in a single operation, all of the surface of the bodily canal at the site which is chosen.

This object is achieved, on the one hand, insofar as the inflatable structure surrounds the catheter body, such that the latter is not in contact with the bodily canal and, on the other hand, insofar as the tube constituting the inflatable structure has a variable diameter, the tube portions defining the cavity intended to contain the active substance having a larger diameter than that of the intermediate tube portion constituting the part intended to hold the membrane, such that the latter portion of the tube is not in contact with the bodily canal.

According to another particular feature of the invention, the tube portion respectively constituting the first and second inflatable elements has a variable-pitch helix configuration defining a first region, consisting of at least two contiguous turns which are intended to bear in leaktight fashion against the internal wall of the bodily canal, and a second region, extending the first and extending as far as the catheter body, said second region forming at least one helix portion whose pitch is greater than that of the helix formed by the turns in the first region, the diameter of the tube in the second region being preferably less than the diameter of the tube in the first region.

This design of the first and second inflatable elements is particularly advantageous since it makes non-traumatic the progress of the catheter when it enters the bodily canal, and, above all, when it is withdrawn therefrom.

In order to facilitate the folding and refolding of the inflatable structure around the catheter body and thus make the latter easier to insert and withdraw, the inflatable structure is preformed, preferably so as to have, seen in cross section relative to the catheter body, the general shape of a spiral which is closed on itself by a series of at least two alternate loops.

According to another particular feature of the invention, in order to further facilitate the refolding after an operation, the aforementioned catheter is provided with means for assisting refolding of the aforementioned inflatable structure after deflation.

According to a first embodiment, these means comprise two elastic threads arranged respectively around the first and second inflatable elements while being connected thereto preferably along a generatrix.

According to another embodiment, these means comprise two substantially cylindrical elastic membranes respectively enclosing the first and second inflatable elements while being connected thereto preferably along a generatrix.

The design of the inflatable structure, combined with the aforementioned means for assisting refolding, guarantees the safety of the catheter according to the invention when it is introduced into the bodily canal and withdrawn therefrom.

BRIEF DESCRIPTION OF THE DRAWINGS

The invention will be better understood, and other objects, features and advantages thereof will emerge more clearly on reading the following explanatory description, made with reference to the appended schematic drawings which are given solely by way of non-limiting example and illustrate a currently preferred embodiment of the invention, and in which.

DETAILED DESCRIPTION OF THE INVENTION

Figure 1:
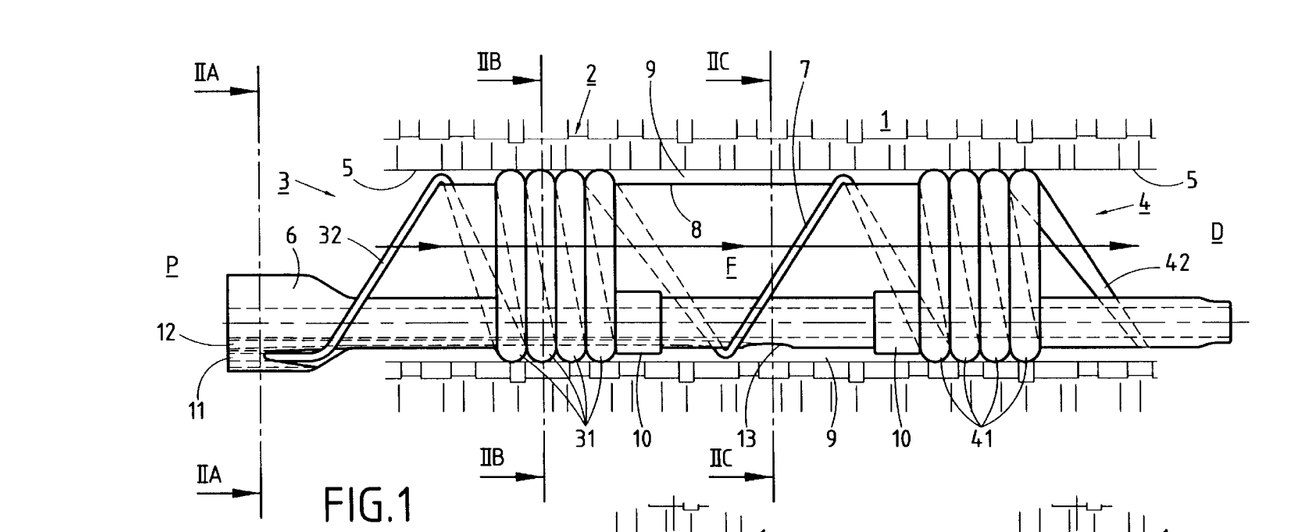
FIG. 1 is a longitudinal schematic view showing the distal end of a catheter according to a currently preferred embodiment of the invention, represented when it is inflated in a bodily canal.

Thus, FIG. 1 represents the distal end of a catheter equipped with an inflatable structure according to a currently preferred embodiment of the invention, when it is inflated in a bodily canal such as, for example, a blood vessel denoted by the reference number 1.

A catheter according to the present invention essentially comprises a catheter body including an elongate tubular element which has a proximal part and a distal part, as well as an inflatable structure generally denoted by the reference number 2, arranged at the distal part of the catheter body.

Only the catheter body part bearing the inflatable structure is represented in FIG. 1.

The proximal part (not represented and denoted by the letter P) of the catheter is located on the left in FIG. 1, while the distal part (not represented and denoted by the letter D) is located on the right.

The inflatable structure 2 generally comprises a preformed tube of variable diameter, having a helicoid turn configuration defining three regions respectively designated by "first", "second" and "third" inflatable element, as well as a membrane fixed to this tube.

In the inflated state, represented in FIG. 1, the first inflatable element 3 and the second inflatable element 4 are axially separated from each other, each bearing in leaktight fashion against the internal wall of the bodily canal 1 and each having a substantially central opening 21.

As can be seen, the tube portion respectively constituting the first and second inflatable elements 3, 4 generally has a variable-pitch helix configuration defining a first region, consisting of at least two contiguous turns which are intended to bear in leaktight fashion, in the inflated state, against the internal wall 5 of the bodily canal 1, and a second region, extending the first and continuing as far as the catheter body 6, said second region forming at least one helix portion, the pitch of which is greater than that of the helix formed by said turns in the first region, the diameter of the tube in the second region being preferably less than the diameter of the tube in the first region.

The number of contiguous turns constituting the first region of the first and second inflatable elements 3, 4 may vary from 2 to several tens, depending in particular on the calibre of the bodily canal and the treatment to be carried out.

By way of example, the first region of the first and second inflatable element 3, 4 may comprise four contiguous turns, respectively denoted by the reference numbers 31 and 41.

The distance between the group of proximal contiguous turns 31 and the group of distal contiguous turns 41 can vary within wide limits, for example between 5 mm and 100 mm.

This distance will be approximately 10 mm in the case of a preventive treatment for restenosis.

The second region of the first and second inflatable elements 3, 4, respectively represented by the reference numbers 32 and 42, forms at least one helix portion whose pitch is greater than that of the helix formed in the first region. This region will generally form substantially one turn.

The tube portions forming the second regions 32 and 42 each extend as far as the catheter body while preferably giving the inflatable structure 2, when seen in cross section, the general shape of a trapezium whose long base lies level with the catheter.

The tube portions 32 and 42 advantageously have a smaller diameter than the tube portions defining the contiguous turns 31 and 41.

By way of example, the diameter of the tube at the portions 32 and 42 may be of the order of 0.5 mm and the diameter of the tube at the contiguous turns 31 and 41 may be of the order of 0.7 mm.

The tube portion defining the third inflatable element 7 which joins together the groups of turns 31 and 41 also has a helix configuration and may comprise one or more turns, depending on the distance separating the groups of turns 31 and 41.

The diameter of the tube portion defining the third inflatable element 7 is less than the diameter of the tube at the turns 31 and 41.

By way of example, the diameter of the tube at the inflatable element 7 may be of the order of 0.5 mm when the diameter of the tube at the turns 31 and 41 is of the order of 0.7 mm.

This results, in particular, in the third inflatable element 7 not being directly in contact with the internal surface 5 of the bodily canal 1, as can be seen in FIG. 1, which constitutes one of the original features of the catheter according to the invention.

The pitch of the helix at the third element 7 will advantageously be greater than that of the helix formed by the groups of turns 31 and 41.

However, this is no more than a preferred embodiment, it being possible for the turns constituting the third inflatable element to be also contiguous with each other and optionally with the turns 31 and 41 of the first and second inflatable elements.

The tube forming the first, second and third inflatable elements may advantageously be made of a thermoplastic such as, for example, a polyamide, an optionally cross-linked polyethylene, a polyurethane or a polyethylene terephthalate.

This tube may be formed from a tube having a constant diameter which is firstly expanded zonally so as to obtain the desired diameters in each of the portions corresponding to the first, second and third inflatable elements.

The tube thus obtained is secondly shaped under pressure so as to obtain the desired final profile (helicoid turns).

The aforementioned design makes it possible to avoid the possible appearance of creases on the turns during inflation. Such creases would in fact impair correct deployment of the inflatable structure 2 and the leaktightness of the cavity 9 at the contiguous turns 31 and 41 of the first and second inflatable elements 3, 4.

The inflatable structure 2 also comprises a membrane 8 which is fixed to the first and second inflatable elements 3, 4 while thus defining with them, when they are inflated:

on the one hand, a substantially cylindrical sleeve joining together in leaktight fashion the central openings 21 of said first and second inflatable elements 3, 4 while thus forming a channel for passage of the bodily fluid; and on the other hand, a substantially annular and leaktight cavity 9, intended to contain one or more therapeutically active substances and laterally bounded, on the proximal side, by the most distal turn of the first inflatable element 3, and on the distal side, by the most proximal turn of the inflatable element 4, and, radially, externally by the internal wall 5 of the bodily canal 1 and internally by the external surface of the membrane 8.

Within the context of the present description and claims, "therapeutically active substance" is understood as meaning any substance or composition having a therapeutic activity. Such a substance can be in various forms such as, for example, a glue, a gel, microspheres, particles or nanoparticles.

The membrane 8 is preferably arranged at the level of the internal diameter of the contiguous turns 31 and 41 of the first and second inflatable elements 3, 4 while being connected thereto preferably irreversibly, for example by adhesive bonding, thermally activated adhesive bonding, welding or dip-coating.

As will be understood, the membrane portion contained between the two groups of contiguous turns 31 and 41 thus defines a tube which is open at its two ends, creating a passage for the flow of the bodily fluid in the direction represented by the arrow F.

By construction, this passage channel for the bodily fluid may have a relatively large diameter, allowing the catheter to be fitted without interrupting the flow of this fluid.

By way of example, the diameter of this channel may be 2.5 mm, in the case of a 3.5 mm artery, which makes it possible to obtain a flow rate of the bodily fluid through the catheter which is greater than 50% of the normal flow rate in the absence of a catheter.

When the tube forming the first, second and third inflatable elements 3, 4, 7 is inflated, the inflatable structure 1 will be deployed and induce a tension on the membrane.

The membrane 8 is generally designed in such a way that the central channel is cylindrical when this membrane is under tension after the first, second and third inflatable elements 3, 4, 7 have been inflated to a predetermined pressure (generally of the order of 6 bar).

The membrane will preferably have a radially elastic behaviour, in order to follow the compliance of the contiguous turns 31, 41.

To this end, the membrane may be made of a material such as a silicone, a polyurethane or a polyamide which can withstand radial stretching.

In a currently preferred embodiment, the membrane is made of polyurethane and can withstand radial stretching equivalent to two times its initial diameter.

The membrane 8 is deployed and shaped under the effect of the inflation of the first, second and third inflatable elements 3, 4, 7, by thus changing from a relatively flexible state to a semi-rigid state, creating a barrier between the tubular passage for the bodily fluid and the aforementioned annular space 9, this space being relatively leaktight with respect to the surrounding medium and being thus capable of serving as a diffusion cavity or pouch for the therapeutically active substance(s) used.

Figure 3:
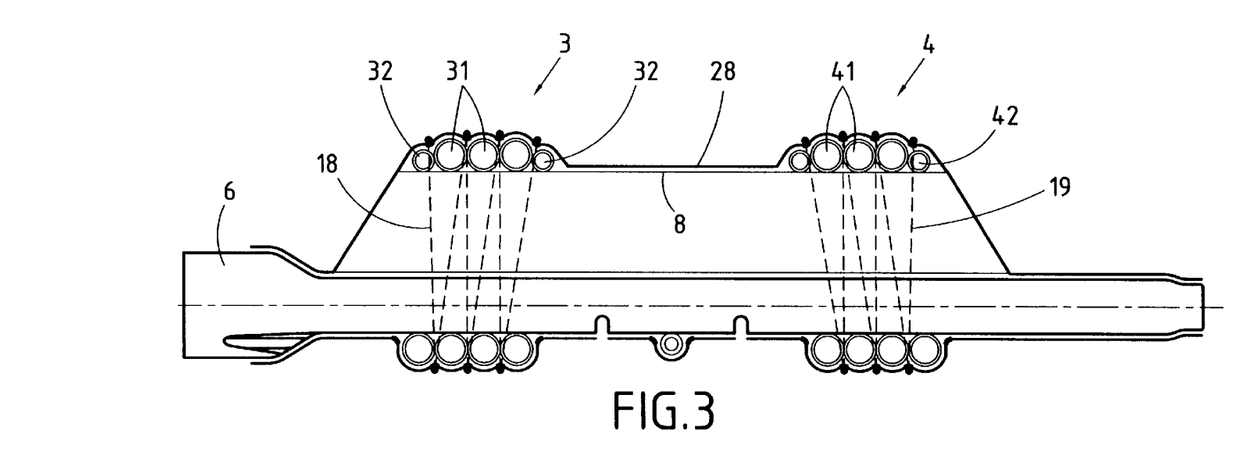
FIG. 3 is a view in longitudinal section illustrating the distal end of a catheter according to another particular embodiment of the invention, including means for assisting refolding of the inflatable structure, which is represented in the inflated state.
Figure 4:
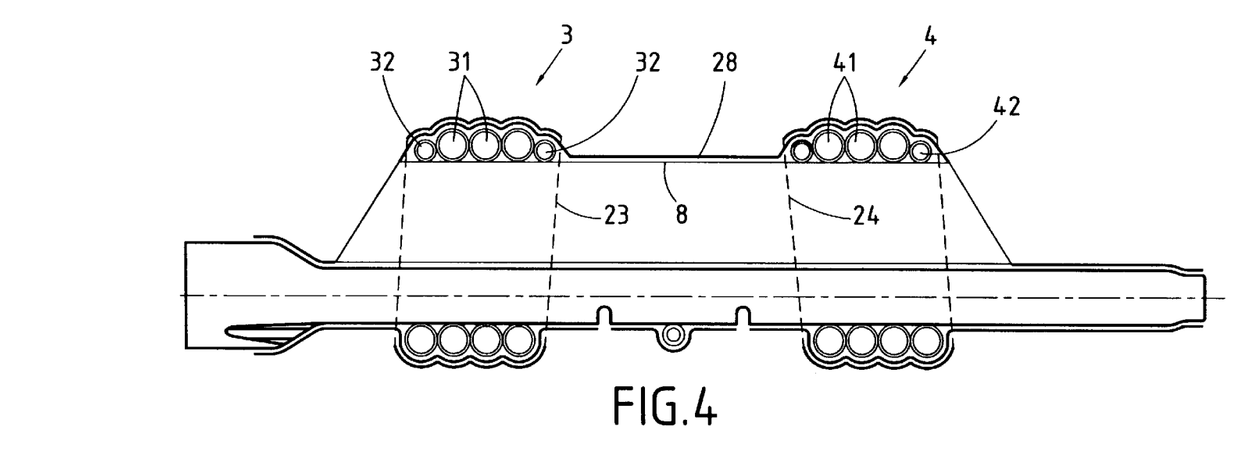
FIG. 4 is a similar view to FIG. 3, of the same catheter including different means for assisting refolding of the inflatable structure.

In the embodiment represented in FIGS. 3 and 4, the inflatable structure 2 includes a second membrane 28, arranged radially and externally relative to the first membrane 8, for enclosing the first and second inflatable elements 3, 4.

The second membrane 28 may optionally be extended as far as the catheter body, in order to enclose the latter partially, as represented in FIGS. 3 and 4.

The second membrane will be connected, for example by adhesive bonding, thermally activated adhesive bonding, welding or dip-coating, to the first and second inflatable elements 3, 4 and, optionally, to the catheter body as well as the first membrane 8.

This particular design makes it possible to obtain better leaktightness of the annular cavity 9 as well as better longitudinal and transverse strength of the inflatable structure 2.

It should further be noted that the first membrane 8 is also fixed, for example by adhesive bonding, thermally activated adhesive bonding, welding or dip-coating, to the third inflatable element 7, the latter contributing to keeping the membrane under tension when the inflatable structure 2 is inflated, in particular preventing the first and second inflatable elements 3 and 4 from moving towards each other.

The role of the third inflatable element is essential for keeping the cross section of the passage channel for the bodily fluid constant during the operation, regardless of the distance separating the first and second inflatable elements 3, 4.

The catheter according to the present invention includes a catheter body, generally consisting of a flexible elongate tubular element, the total length of which may be approximately 135 cm and the diameter variable from 0.70 mm to 3 mm, depending on the desired application.

This diameter will advantageously be approximately 1 mm in the case of the preventive treatment of restenosis.

The catheter body preferably consists of a plurality of parts, with different diameters, made of materials which have different flexibilities.

The proximal part has a total length of approximately 110 cm and the distal part has a total length of approximately 25 cm.

The distal end, represented in FIG. 1 and intended to support the inflatable structure, is advantageously stretched over a length slightly greater than the length of the portion of the bodily canal to be treated, for example by approximately 3 cm in this particular case.

The catheter body may be made, for example, of a material such as a semi-rigid thermoplastic like, for example, a high-density polyethylene, a polyamide, or a copolymer of the type PEBAX® marketed by the company ATOCHEM.

Figure 2A:
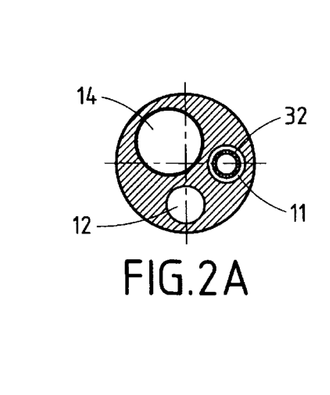
FIG. 2A is a view in cross section along the line IIA—IIA in FIG. 1.
Figure 2B:
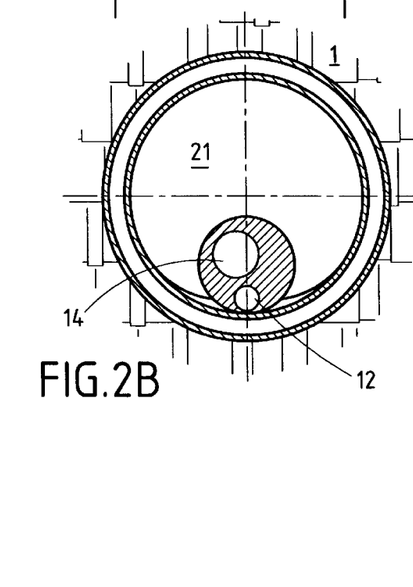
FIG. 2B is a view in cross section along the line IIB—IIB in FIG. 1.
Figure 2C:
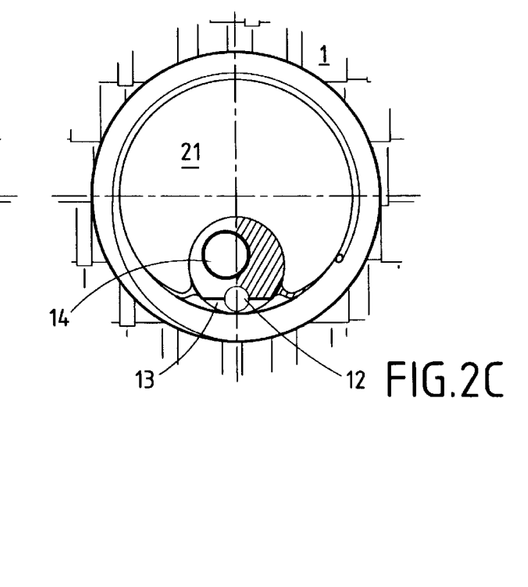
FIG. 2C is a view in cross section along the line IIC—IIC in FIG. 1.

The catheter body, and this constitutes an original feature of the invention, is arranged inside the aforementioned inflatable structure, that is to say inside the passage channel for the bodily fluid, as shown in particular by FIG. 2B and 2C.

This has the particular result that the catheter body is not in direct contact with the internal wall 5 of the bodily canal 1, in particular at the site to be treated, which constitutes a determining advantage over the state of the art catheter described in document EP-0.526.102. 12

According to the invention, the catheter body includes a first internal channel 11 which communicates, on the one hand, with the tube constituting the first, second and third inflatable elements 3, 4, 7 and, on the other hand, with a means (not represented) making it possible to inflate and deflate this tube.

In the currently preferred embodiment, the internal channel 11 and the tube constituting the first, second and third inflatable elements 3, 4 and 7 communicate via the tube portion 32 defined above.

The catheter body further comprises a second internal channel 12 which communicates, on the one hand, with the aforementioned annular cavity 9, and on the other hand, with a supply source of fluid containing one or more pharmacologically active substances.

In the currently preferred embodiment, the second internal channel 12 of the catheter body and the aforementioned cavity 9 communicate through one or more diffusion orifices 13 made in the catheter body and in the membrane 8, preferably in the form of notches extending longitudinally and having a length of approximately 2 mm.

In the embodiment represented in FIG. 1, there is only one single diffusion orifice 13, made in the form of a notch with a length of 2 mm and having a diameter of 0.2 mm.

The particular form of this notch allows uniform diffusion of the pharmacologically active substance in the annular cavity 9.

It should be noted that, by virtue of this particular form, the pharmacologically active substance diffuses through the orifices 13 in the form of drops which are non-traumatising for the wall of the morphological canal, which also constitutes an advantage.

The wall of the canal is therefore progressively affected by the pharmacologically active substance, it being possible for the diffusion rate and therefore the pressure inside the annular cavity 9 to be subsequently increased substantially, if necessary.

According to a particular feature, the external surface of the second membrane 28 may be porous in the part contained between the first and second inflatable elements 3, 4, allowing even more uniform and even less traumatising diffusion of the pharmacologically active substance inside the annular cavity 9.

Figure 7:
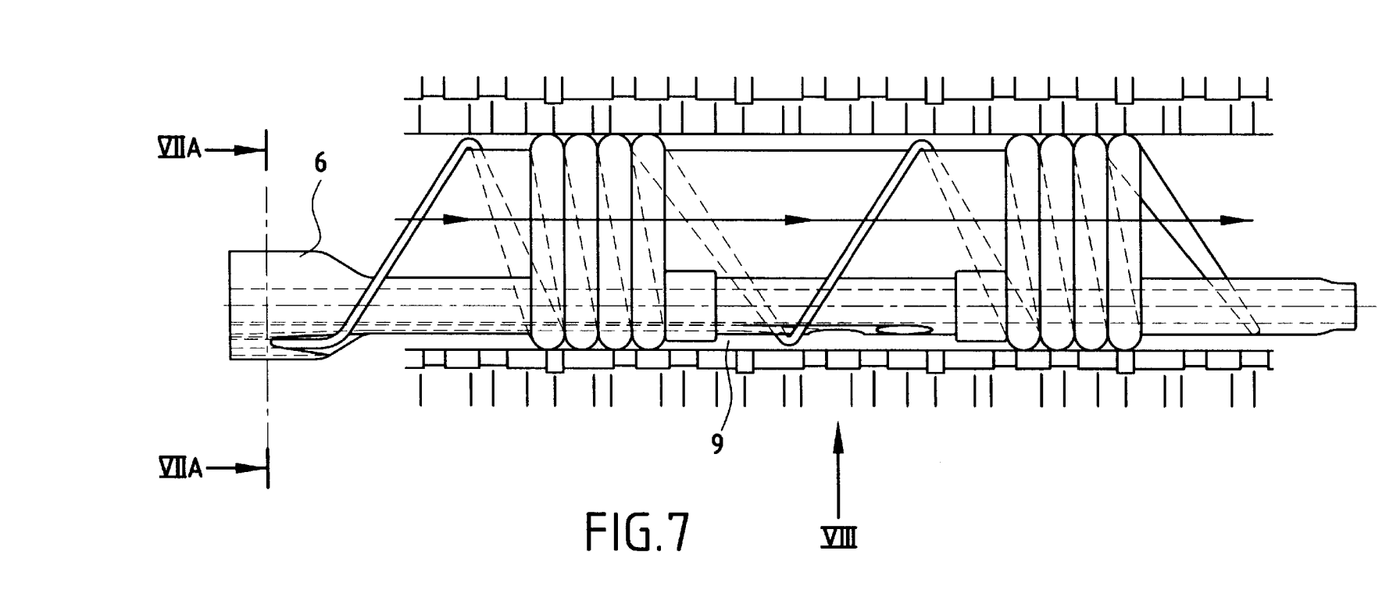
FIG. 7 is a longitudinal schematic view showing the distal end of a catheter according to another embodiment of the invention, which has a second and third internal channel.

The catheter body may further comprise a third internal channel 12A, which is independent from the second internal channel 12, and which communicates on the one hand with the aforementioned annular cavity 9, and on the other hand, either with a supply source of fluid optionally containing one or more active substances identical or different to the active substance(s) which can be carried by the second internal channel 12, or with a suction device.

Figure 7A:
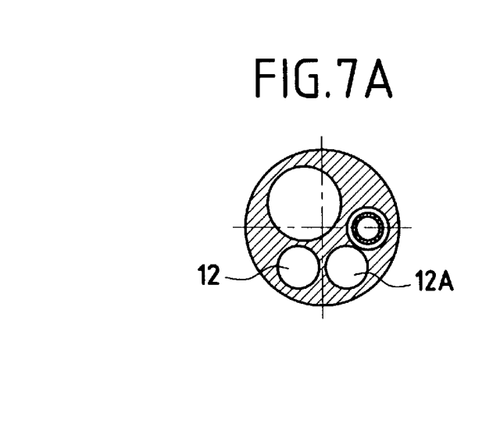
FIG. 7A is a view in cross-section along the line A—A in FIG. 7.
Figure 8:
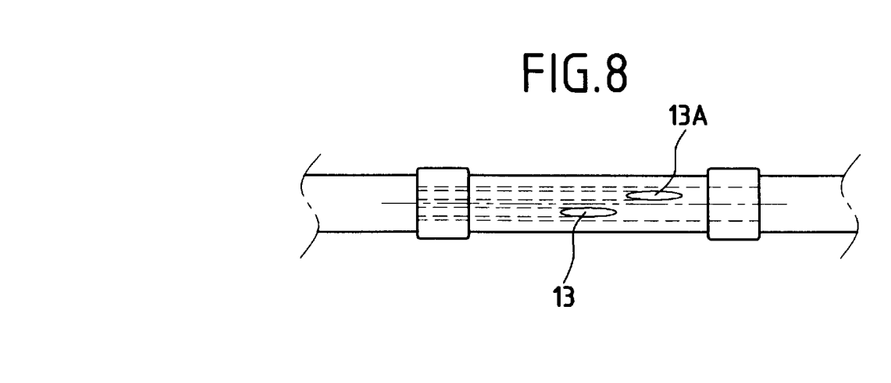
FIG. 8 is a partial view of the catheter body according to view F in FIG. 7.

In the currently preferred embodiment, represented in FIGS. 7, 7A and 8, the communication between the third internal channel 12A of the catheter body and the aforementioned cavity 9 is made via one or more diffusion orifices 13A which preferably have the same conformation as the aforementioned diffusion orifices 13.

The suction device connected to the eventual third internal channel 12A may serve, in the context of the treatment of aneurysms for example, to allow evacuation of the liquid contained in the aneurysm pouch, and in this case, the second internal channel 12 allows filling said aneurysm pouch by means of an adequate therapeutically active substance.

The catheter body may further comprise a fourth internal channel 14, constituting a passageway for a guide wire (not represented) or any other probe.

The catheter used in the context of the present invention may be of the "quick change" type, that is to say that the guide wire will pass through its body only over a small portion of its length, corresponding substantially to the distal part. In this case, in the proximal part, the catheter body may include only the first and second aforementioned internal channels.

The catheter may also be of a type known by the term "over the wire", that is to say that the guide will pass through the body over its entire length. In this case, it will be necessary to provide the aforementioned third channel, constituting the passageway for the guide.

The catheter may also be further provided with a core with a high elastic modulus, such as defined in the document WO 95/28197, extending along the catheter body substantially as far as the distal end, in order to allow optimum transmission of the thrust exerted by the doctor on the proximal end of the catheter when it is introduced into the bodily canal.

In order to allow the catheter according to the present invention to be introduced into and withdrawn from a bodily canal, it is necessary for the catheter body to have, in particular at the distal part bearing the aforementioned inflatable structure, a reduced diameter when the latter is deflated.

Figure 6:
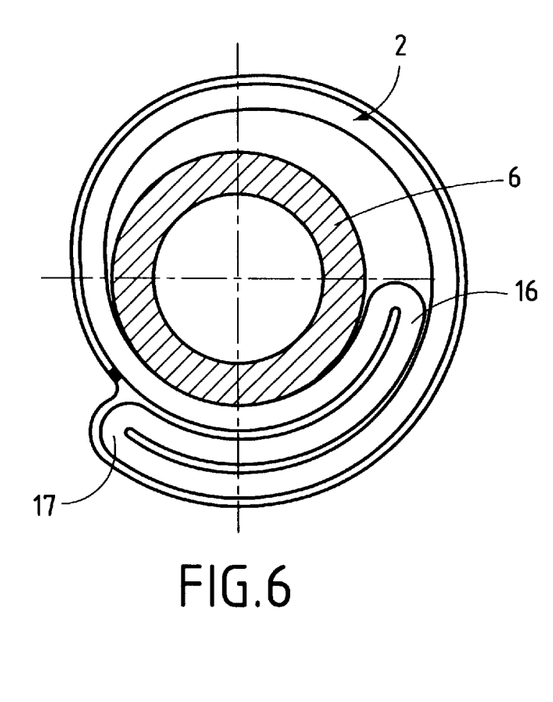
FIG. 6 is a view in cross section of the same catheter, the inflatable structure being in the deflated and refolded state

In order to facilitate folding of the inflatable structure about the catheter body and thus to make the latter easier to introduce into the bodily canal the inflatable structure is preformed, for example with the structure represented in FIG. 6, this preforming further giving the inflatable structure a "memory" facilitating its refolding and thus making it easier to withdraw the catheter after the operation.

As shown by FIG. 6, the inflatable structure can thus be formed, for example under pressure, in order to have, seen in cross section relative to the catheter body, the general shape of a turn which is closed on itself by two alternate loops 16, 17.

In order to further facilitate the refolding of the inflatable structure 2, a catheter according to the invention may further be provided with means for assisting refolding of the aforementioned inflatable structure after it is deflated.

Figure 5:
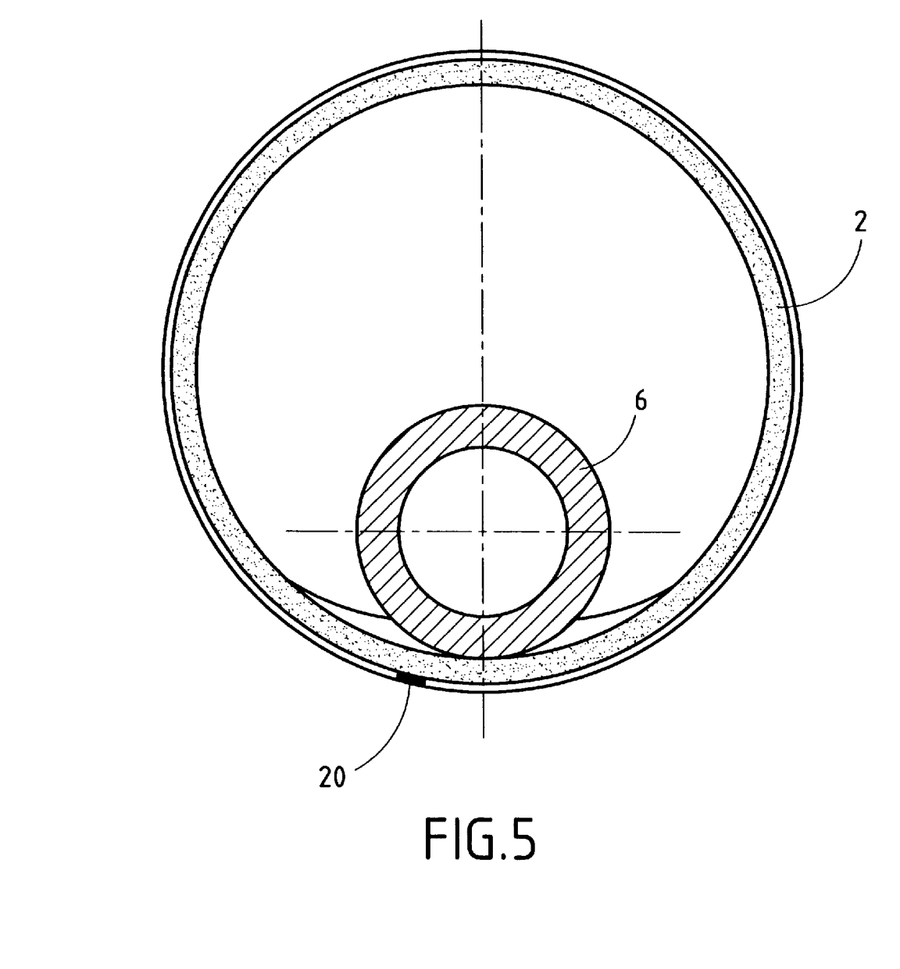
FIG. 5 is a schematic view in cross section of a catheter according to the present invention, provided with means for assisting refolding and represented in the inflated state.

According to a first embodiment, represented in FIG. 3, these means for assisting refolding comprise two elastic threads 18, 19, arranged respectively around the first and second inflatable elements 3, 4, while being connected thereto preferably along a generatrix 20 (see FIG. 5).

This connection may be made, for example, by adhesive bonding, thermally activated adhesive bonding, welding or dip-coating.

The aforementioned elastic elements may be made of a highly elastic material such as, for example, latex or some polyurethanes or silicones.

According to another embodiment, represented in FIG. 4, the means for assisting refolding comprise two substantially cylindrical elastic membranes 23, 24, respectively enclosing the first and second inflatable elements 3, 4, being also connected thereto preferably along a generatrix 20 (see FIG. 5).

As will be understood, the elements for assisting refolding will act, after the inflatable structure 2 is deflated, by exerting an elastic return force which facilitates the refolding of this structure 2 into its initial position, as represented in FIG. 6.

This particular feature gives the catheter of the invention greater safety when it is introduced into and withdrawn from the bodily canal.

The way in which the catheter according to the invention is used can be deduced easily from its structure which has just been described.

Before the catheter is introduced into the bodily canal, the channel 12 of the catheter is filled with a physiological saline solution in order to remove all the air bubbles present in this channel.

The catheter, provided with its inflatable structure in the deflated state, and refolded, is introduced in the traditional way, for example using a guide wire, into a morphological canal such as a blood vessel and is positioned using radio-opaque markers 10 (see FIG. 1) at the location of the site intended to be treated, for example the site of a stenosis dilated by angioplasty.

When the catheter is positioned in this way, the inflatable structure 2 is supplied through the inflation conduit 11 up to a pressure equal to approximately a fraction of the normal working pressure (approximately 2 bar).

During this preliminary inflation, the inflatable structure 2 will be deployed and will cause the membrane 8 to be tensioned.

The annular cavity 9 is then supplied, via the channel 12, with a small quantity (of the order of 1 cm$^3$) of a fluid containing one or more active substances in order to replace the physiological saline solution present in said channel. The maximum pressure during this operation is 1 bar.

The inflatable structure is then brought progressively to the desired sealing pressure which may be of the order of 4 to 14 bar.

The therapeutically active substance is then introduced into the leaktight annular cavity 9 at the desired rate.

A number of therapeutically active substances may be administered in the context of the present invention, such as, for example, antithrombins, converting enzyme inhibitors, vasodilators, lipidemic agents or even some proto-oncogenes.

The catheter which has just been described is particularly advantageous since it permits very accurate diffusion of the various therapeutically active substances at desired concentrations for a predetermined length of time.

In addition, the particular design of this catheter allows all of the surface of the bodily canal to be treated in a single operation at the chosen site.

The catheter which has just been described may also be used to isolate a segment of the wall of a bodily canal, especially for treating an aneurysm, for assisting a surgical operation upon said wall segment thus isolated, such as, for example a by-pass, or even for performing a selective embolisation.

In the particular case of the treatment of aneurysms, the catheter according to the present invention enables isolating the malformation of the rest of the blood flow, so as to be able to treat the blood flow more effectively and more safely than by existing means. The risk of accidental embolisation is thus considerably reduced.

We claim:

1. A catheter for introduction into a bodily canal in which a fluid flows, in order to deliver thereto, in a localised region, a therapeutically active substance carried by a second fluid, of the type comprising:

a catheter body including an elongate tubular element having a proximal part and a distal part;

an inflatable structure, arranged at the distal part of said catheter body and including:

a first inflatable element and a second inflatable element which, when inflated:
are axially separated from one another;
each bear in leaktight fashion against the internal wall of said bodily canal; and
each has a substantially central opening;

a membrane, fixed to said first and second inflatable elements and defining with them, when they are inflated:
a substantially cylindrical sleeve, joining together the central openings of said first and second inflatable elements, in leaktight fashion, thus forming a channel for passage of the bodily fluid; and
a substantially leaktight cavity, capable of containing said therapeutically active substance and defined by said first and second inflatable elements, by the external surface of said membrane and by the internal surface of the bodily canal;

a third inflatable element, arranged between said first and second inflatable elements, designed to keep said membrane in position when it is inflated;

said catheter body including a first internal channel which communicates with said first, second and third inflatable elements and has a means for inflating and deflating said elements; a second internal channel which communicates with said cavity and with a supply source of fluid containing said pharmacologically active substance, wherein said first, second and third inflatable elements are made in a single preformed part, consisting of a helically wound tube, said third element consisting of at least one turn of said helically wound tube, the diameter of said tube at the portion constituting said third element being less than the diameter of said tube at the tube portions which respectively constitute said first and second elements and are intended to bear against the internal wall of said bodily canal; and wherein said catheter body is arranged inside the winding of said helically wound tube.

2. The catheter as claimed in claim 1, wherein the tube portion respectively constituting the first and second inflatable elements has a variable-pitch helix configuration defining a first region, consisting of at least two contiguous turns which are adopted to bear in leaktight fashion against the internal wall of the bodily canal, and a second region, extending the first and continuing as far as the catheter body, said second region forming at least one helix portion whose pitch is greater than that of the helix formed by the turns in the first region.

3. The catheter as claimed in claim 2, wherein the diameter of the tube in said second region is less than the diameter of the tube in said first region.

4. The catheter as claimed in claim 1, wherein said inflatable structure is preformed.

5. The catheter as claimed in claim 1, wherein said inflatable structure is preformed so as to have, seen in cross section relative to the catheter body, the general shape of a spiral which is closed on itself by a series of at least two alternate loops.

6. The catheter as claimed in claim 1, which comprises means for assisting refolding of said inflatable structure after deflation.

7. The catheter as claimed in claim 6, wherein said means for assisting refolding comprise two elastic threads arranged respectively around the first and second inflatable elements while being connected thereto.

8. The catheter as claimed in claim 6, wherein said means for assisting refolding comprise two elastic threads arranged respectively around the first and second inflatable elements while being connected thereto along a generatrix.

9. The catheter as claimed in claim 6, wherein said means for assisting refolding comprise two substantially cylindrical elastic membranes respectively enclosing the first and second inflatable elements while being connected thereto.

10. The catheter as claimed in claim 6, wherein said means for assisting refolding comprise two substantially cylindrical elastic membranes respectively enclosing the first and second inflatable elements while being connected thereto along a generatrix.

11. The catheter as claimed in claim 1, wherein said membrane is arranged at the level of the internal diameter of the contiguous turns of the first and second inflatable elements while being connected thereto.

12. The catheter as claimed in claim 1, wherein said membrane is arranged at the level of the internal diameter of the contiguous turns of the first and second inflatable elements while being connected thereto irreversibly by a means selected from the group consisting of adhesive bonding, thermally activated adhesive bonding, welding, and dip-coating.

13. The catheter as claimed in claim 11, wherein said membrane is made of a material which can withstand radial stretching.

14. The catheter as claimed in claim 13, wherein said material which can withstand radial stretching is selected from the group consisting of silicone, polyurethane, and polyamide.

15. The catheter as claimed in claim 1, wherein said inflatable structure includes a second membrane, arranged radially and externally relative to the first membrane and enclosing said first and second inflatable elements.

16. The catheter as claimed in claim 1, wherein said second internal channel of the catheter body and said cavity communicate via at least one diffusion orifice which are in the form of longitudinal notches which diffuse the therapeutically active substance in the form of drops which are non-traumatising for the wall of the bodily canal.

17. The catheter as claimed in claim 1, wherein said catheter body includes a third internal channel, independent from said second internal channel, which communicates with said cavity, and with a supply source of fluid.

18. The catheter as claimed in claim 1, wherein said catheter body includes a third internal channel, independent from said second internal channel, which communicates with said cavity, and with a supply source of fluid containing a therapeutically active substance.

19. The catheter as claimed in claim 1, wherein said catheter body includes a third internal channel, independent from said second internal channel, which communicates with said cavity, and with a suction device.

* * * * *